United States Patent [19]

McCahon et al.

[11] Patent Number: 5,080,469
[45] Date of Patent: Jan. 14, 1992

[54] OPTICAL LIMITER INCLUDING OPTICAL CONVERGENCE AND ABSORBING BODY WITH INHOMOGENEOUS DISTRIBUTION OF REVERSE SATURABLE MATERIAL

[75] Inventors: Stephen W. McCahon, Newbury Park; Lee W. Tutt, Thousand Oaks, both of Calif.

[73] Assignee: Hughes Aircraft Company, Los Angeles, Calif.

[21] Appl. No.: 502,160

[22] Filed: Mar. 29, 1990

[51] Int. Cl.$^5$ .......................... G02B 5/23; G02B 9/00; H01S 3/113

[52] U.S. Cl. ...................................... 359/241; 372/11; 359/738

[58] Field of Search .................... 350/354, 448; 372/11

[56] References Cited

U.S. PATENT DOCUMENTS

| | | | |
|---|---|---|---|
| 3,620,597 | 11/1971 | Schwartz et al. | 350/354 |
| 4,657,345 | 4/1987 | Gordon | 350/311 |
| 4,723,248 | 2/1988 | Harter et al. | 372/25 |
| 4,890,075 | 12/1989 | Pohlmann | 330/4.3 |

FOREIGN PATENT DOCUMENTS 99524 2/1984 European Pat. Off.

OTHER PUBLICATIONS

Applied Optics (Swope and Koester) 5/1965, pp. 523–526, vol. 4, No. 5, "Eye Protection Against Lasers".

"Optical Limiting in Solutions of Metallo-phthalocyanines and Naphthalocyanines", D. R. Coulter, et al., SPIE vol. 1105, Materials for Optical Switches, Isolators, and Limiters (1989), pp. 42–51.

Hagan et al., "Passive Broadband High Dynamic Range Semi-Conductor Limiters", SPIE vol. 1105, Materials for Optical Switches, Isolators, and Limiters (1989), pp. 103–113.

Tutt et al., "Optical Limiting Via Reverse Saturable Absorption in Metal Cluster Compounds", CLEO '89/Wednesday Morning, pp. 158–160, Apr. 26, 1989.

K. P. J. Reddy, "An Analysis of Pulse Propagation Through a Saturable Absorber Having Excited-State Absorption", Optical and Quantum Electronics 19 (1987), pp. 203–208.

Primary Examiner—Rolf Hille
Assistant Examiner—Robert P. Limanek
Attorney, Agent, or Firm—V. D. Duraiswamy; W. K. Denson-Low

[57] ABSTRACT

A lens (12) converges a light beam (16) into a light absorbing body (14) having a material which exhibits reverse saturable optical absorption distributed therein with a non-uniform concentration. The concentration is maximum at the focal point (20) of the converged light beam (16), and decreases toward the lens (12) with a distribution selected in correspondence with the optical gain of the converged light beam (16) to limit the local fluence of the light beam (16) propagating through the absorbing body (14), and the output energy of the light beam (16), to predetermined maximum values. The non-uniform concentration further produces a self-protecting effect by causing the region of maximum fluence of the converged light beam (16) to shift toward the lens (12), thereby protecting the region of highest optical gain and highest molecular concentration, as the input energy of the light beam (16) increases.

22 Claims, 7 Drawing Sheets

LEGEND
□ = GRADED DISTRIBUTION
♦ = UNIFORM DISTRIBUTION

OPTICAL LIMITER INCLUDING OPTICAL CONVERGENCE AND ABSORBING BODY WITH INHOMOGENEOUS DISTRIBUTION OF REVERSE SATURABLE MATERIAL

GOVERNMENT RIGHTS

This invention was made with Government support under Contract No. N62269-87-C-0263 awarded by the Department of the Navy. The government has certain rights in this invention.

BACKGROUND OF THE INVENTION

1. Field of the Invention

The present invention generally relates to the field of optics, and more particularly to the protection of eyes, sensors, and other objects from high intensity light.

2. Description of the Related Art

High intensity light sources, such as lasers, electric arc welders, and direct sunlight, are potentially damaging to the human eye as well as to optoelectronic sensors and other equipment used in technological environments. Workers in such environments have conventionally worn eye protection glasses or goggles including lenses formed of a material having a high level of optical absorption for all values of incident light intensity. The lenses in welding goggles and face plates, for example, absorb so much light under normal conditions that practically nothing can be seen through them until the welding arc is struck, requiring them to be constantly moved into and away from their protecting position in front of the worker's eyes.

Optical limiters whose level of absorption increases as the incident light intensity increases have been developed using materials which exhibit reverse saturable absorption (RSA). These materials have conventionally been dissolved in a liquid or incorporated into a solid with a uniform concentration of molecules. The principles of RSA are outlined in a paper entitled "An analysis of pulse propagation through a saturable absorber having excited-state absorption", by K. Reddy, in Optical and Quantum Electronics 19 (1987), pp. 203-208.

Optical limiting action can be enhanced by converging an input light beam into the material, as described in a paper entitled "PASSIVE BROADBAND HIGH DYNAMIC RANGE SEMICONDUCTOR LIMITERS", by D. Hagan et al, in SPIE vol. 1105 Materials for Optical Switches, Isolators, and Limiters (1989), pp. 103-113. The material reported was a semiconductor, polycrystalline ZnSe.

Optical limiters using reverse saturable absorbers in the past have all had a uniform concentration of molecules throughout the extent of the absorbing material. The disadvantage of this, whether or not the input light beam is converged into the material, is that many of the molecules are outside the focal region (high fluence region), and will act as normal linear absorbers and not contribute to the optical limiting action. This is because the local fluence, or energy flux per unit area, in the material outside the focal region, is below the threshold at which the reverse saturable absorption "turns on", and involvement of the triplet levels begins to occur as discussed above.

SUMMARY OF THE INVENTION

The present invention provides an improved optical limiter including a material which exhibits reverse saturable absorption, and an optical converging lens for converging an input light beam whose intensity or energy is to be limited, into the material. The absorbing material has an inhomogeneous concentration gradient or distribution, which is selected in correspondence with the optical gain of the converging lens, to utilize more effectively the non-linear properties of the material for optical limiting applications by extending the power handling capabilities due to a self-protecting action which is enhanced by the concentration distribution.

The concentration distribution increases the power handling capabilities of the material, which in turn enables a better limiting action to occur. This is due to the non-linear absorption acting in such a manner as to protect from damage the regions of material which have the highest concentration of molecules, and which would, without the proper distribution of non-linear absorbing molecules, be subjected to catastrophic fluence levels. The contrast and switching thresholds are improved because more of the non-linear material is located at regions of high fluences, and therefore more are activated or switched to the highly absorbing state for a given input energy.

More specifically, the lens converges a light beam into a light absorbing body having a material which exhibits reverse saturable optical absorption distributed therein with a non-uniform concentration. The concentration is maximum at the focal point of the converged light beam, and decreases toward the lens with a distribution selected in correspondence with the type of molecule used and the optical gain of the converged light beam to limit the local fluence of the light beam propagating through the absorbing body, and the output energy of the light beam, to predetermined maximum values. The non-uniform concentration further produces a self-protecting effect by causing the region of maximum fluence of the converged light beam to shift toward the lens, thereby protecting the region of highest optical gain and highest molecular concentration, as the input energy of the light beam increases.

These and other features and advantages of the present invention will be apparent to those skilled in the art from the following detailed description, taken together with the accompanying drawings, in which like reference numerals refer to like parts.

DESCRIPTION OF THE DRAWINGS

FIG. 3b is similar to FIG. 3a, but illustrates propagation with the linear and reverse saturation turned on;

DETAILED DESCRIPTION OF THE INVENTION

Figure 1:
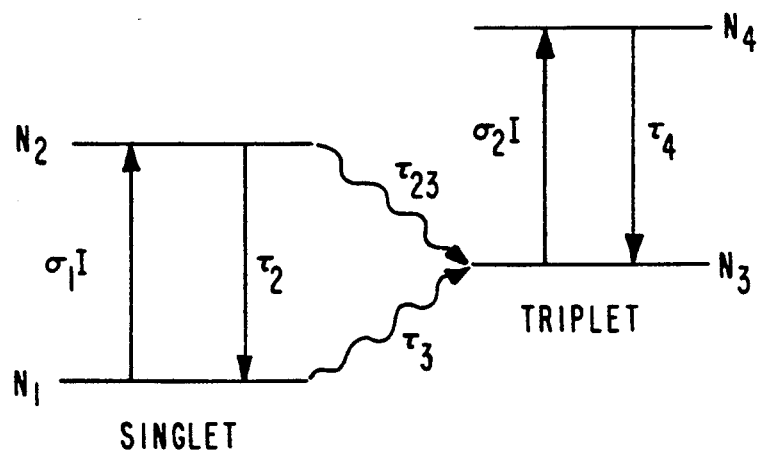
FIG. 1 is a diagram illustrating reverse saturable absorption as applicable to the present invention.

RSA in organo-metallic compounds such as the metal cluster compounds referenced above involve four energy levels, including two singlet states or levels having molecular concentrations $N_1$ and $N_2$, and two triplet states or levels having molecular concentrations $N_3$ and $N_4$, as illustrated in FIG. 1. Initially the molecules are in the ground state, which is the singlet level $N_1$. When irradiated by light of an appropriate wavelength, some of the molecules are excited by linear absorption to the higher singlet level $N_2$, where they can relax to either the original ground level $N_1$ or to the lower triplet level $N_3$. The triplet level $N_3$ has a slower decay rate back to the singlet level $N_1$ than from the singlet level $N_2$ to $N_1$, and a significant proportion of the molecules accumulate in the level $N_3$ as the incident radiation increases.

If the absorption cross-section $\sigma_2$ between the triplet levels $N_3$ and $N_4$ is greater than the absorption cross-section $\sigma_4$ between the singlet levels $N_1$ and $N_2$, then the condition $N_3\sigma_2 > N_1\sigma_1$ can occur and the larger triplet absorption begins to dominate the absorption in the material. As the incident radiation increases beyond the condition at which the triplet absorption begins to dominate, the excess radiation is absorbed by the increasingly populated triplet state and the level of output energy is fixed at a certain level. This non-linear behavior is known as optical limiting.

This four level system can be described mathematically by the following four coupled linear differential state equations, for incident light intensity $I(z,t)$ and $N(z,t)$, where $N$ is the proportion of the total population of molecules in a particular energy level:

$$dN_2/dt = \sigma_1(I/h\nu)(N - N_2 - N_3 - N_4) - N_2/\tau_2(1 + 1/BR)$$

$$dN_3/dt = -\sigma_2 I N_3 - N_3/\tau_3 + N_4/\tau_4 + N_2/\tau_{23}$$

$$dN_4/dt = \sigma_2 I N_3 - N_4/\tau_4$$

$$N = N_1 + N_2 + N_3 + N_4$$

and a differential absorption equation $$dI/dz = \sigma_1 I(N - N_2 - N_3 - N_4) - \sigma_2 I N_3$$

where h is Planck's constant, $\nu$ is the frequency of the light beam, $\tau_1$ to $\tau_4$ are relaxation time constants, and BR is a branching ratio $\tau_2/\tau_{23}$.

Figure 2:
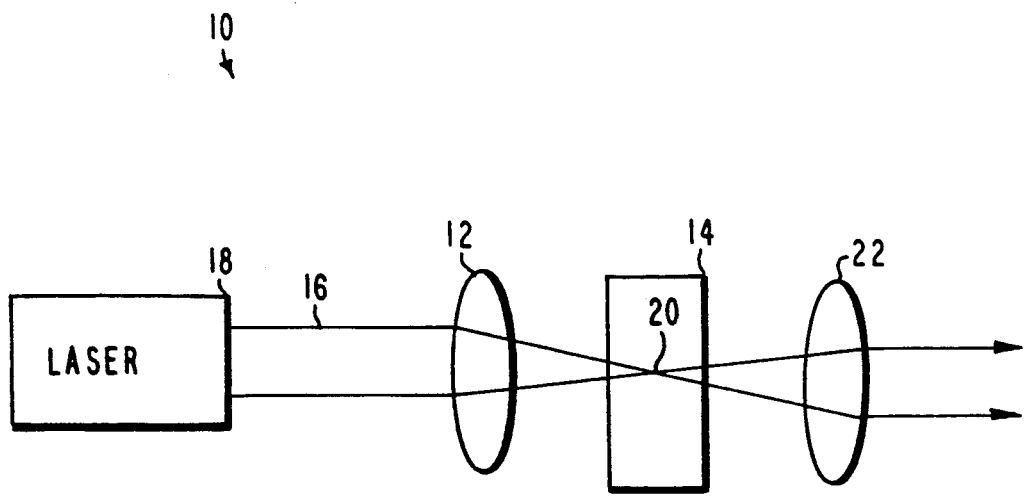
FIG. 2 is a schematic diagram illustrating an optical limiter embodying the invention.

Referring now to FIG. 2 of the drawing, an optical limiter embodying the present invention is generally designated as 10, and includes an optical converging lens 12 and a light absorbing body 14. The lens 12 is designed to converge an input light beam 16 from a light source 18 such as a laser to a focal point or beam waist 20 in the body 14. The focal length of the lens 12 is selected to produce a value of optical gain in the body 14 which corresponds to a non-uniform distribution of molecules of a reverse saturable material therein.

The light source 18 need not have any specific configuration, and may be constituted by light reflected from an object. If desired, an additional converging lens 22 may be provided to re-collimate the light beam which was converged into the body 14 by the lens 12. Although not illustrated, it is further within the scope of the invention to provide additional lenses and light absorbing bodies at desired points downstream of the body 14.

In accordance with the present invention, the reverse saturable material in the body 14 has a non-uniform concentration gradient or distribution which will be described with reference to FIGS. 3a to 6b. These are computer generated graphs based on the properties of iron tricobalt deca-carbonyl bistrimethyl phosphine, an exemplary organometallic RSA material. However, it will be understood that the invention is not limited to the use of any particular material, and may be practiced using any appropriate composition of matter which exhibits non-linear absorption through reverse saturation or any other mechanism.

Figure 3A:
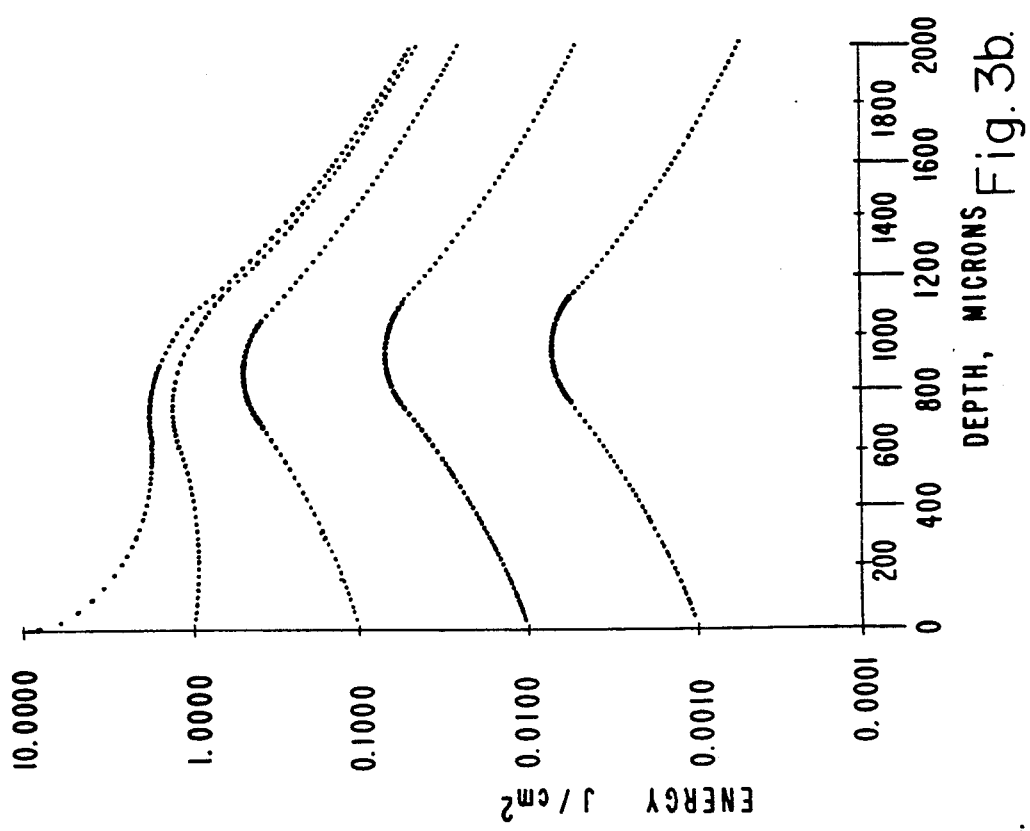
FIG. 3a is a graph illustrating propagation of a collimated light beam through a reverse saturable light absorbing material with the linear and reverse saturation turned off and an optical gain factor of 10.
Figure 3B:
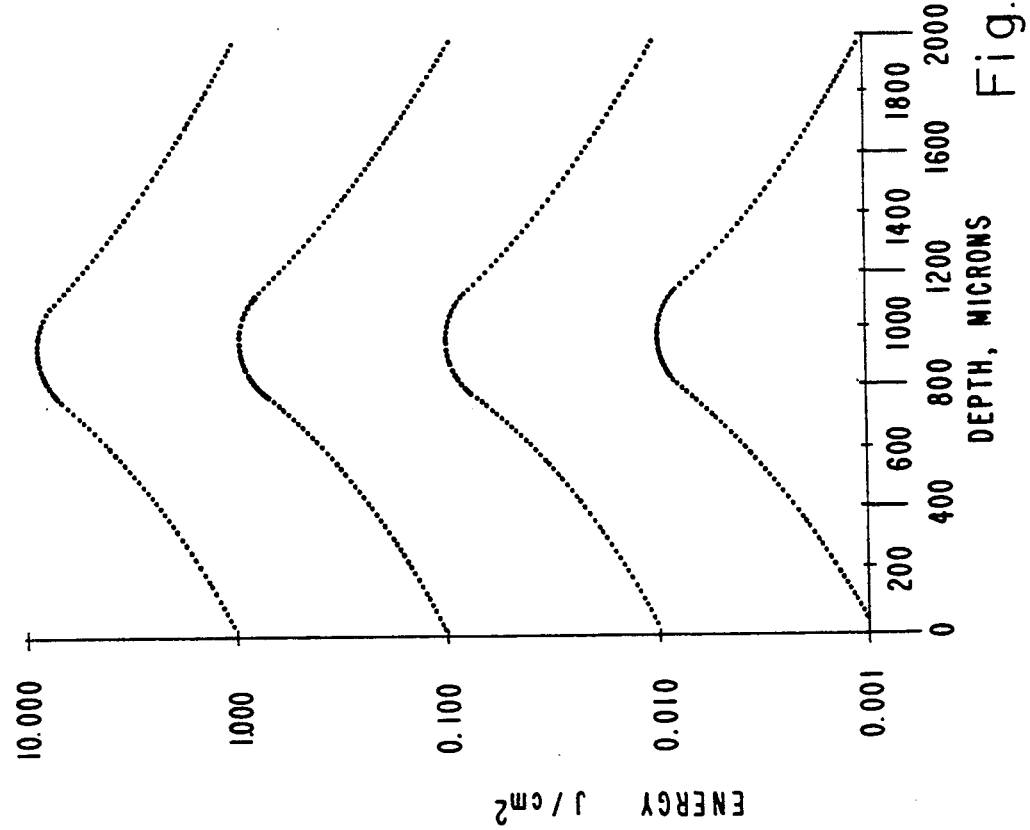

FIGS. 3a and 3b illustrate the effects of non-linear absorption on the energy in a converging light beam in a reverse saturable material having a uniform concentration of molecules. FIG. 3a plots the local energy (which is proportional to the fluence) as a function of depth into the material for five different input energy levels with the linear and non-linear absorption turned off. This provides a reference, and corresponds to the propagation of a light beam in empty space. The optical gain produced by the beam convergence is assumed to have a factor of 10. Thus, the fluence at the focal point or beam waist in the center of the material is 10 times the fluence at the input edge. The linear absorption of the material, which constitutes all of the absorption at low light levels with the material turned off, is assumed to be 50%.

In FIG. 3b, the non-linear absorption is turned on for the same optical configuration. As the input energy increases from 1 mJ/cm$^2$, to 10J/cm$^2$, the output energy converges to a clamped or limited value of approximately 75 mJ/cm$^2$. This is due to the optical limiting effect. It will be noted, however, that the clamped value is approximately 1.5% of the value in FIG. 3a for linear absorption. Also, the maximum value of energy does not exceed 10J/cm$^2$ at any point inside the sample, even though the gain of 10 would make the energy at the center 100J/cm$^2$ without absorption, and 75J/cm$^2$ with linear absorption.

Figure 4A:
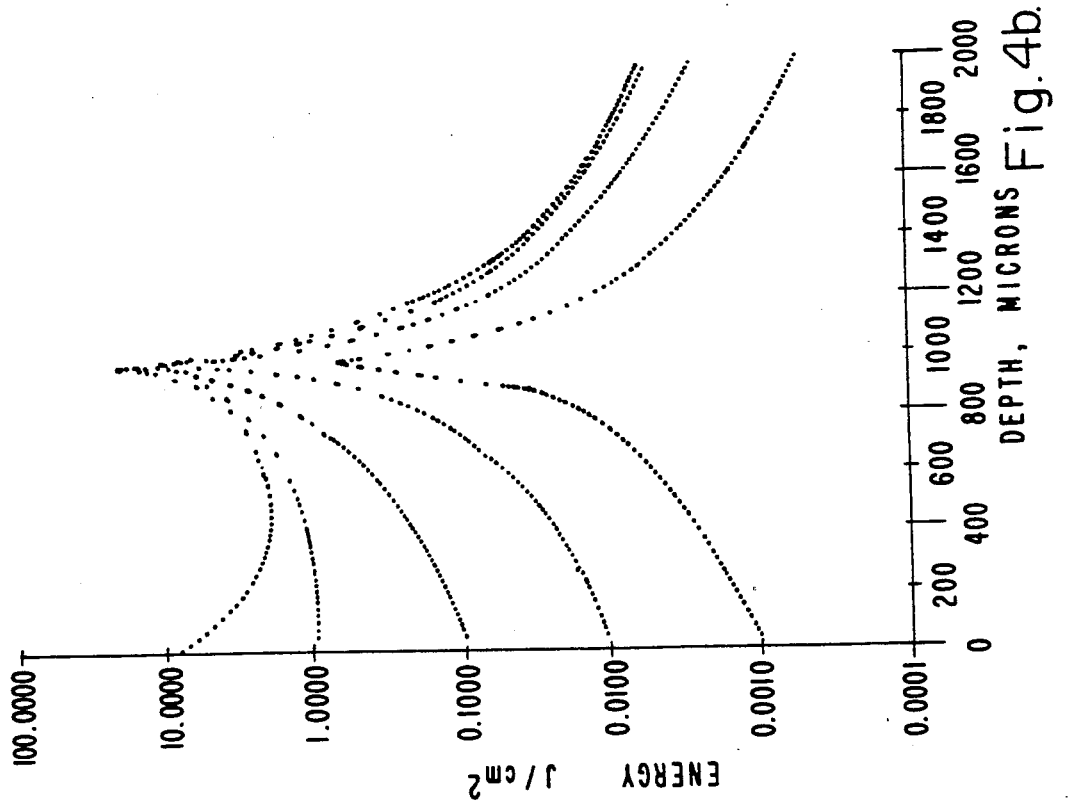
FIGS. 4a and 4b are similar to FIG. 3b, but illustrate optical gain factors of 500 and 900 respectively.
Figure 4B:
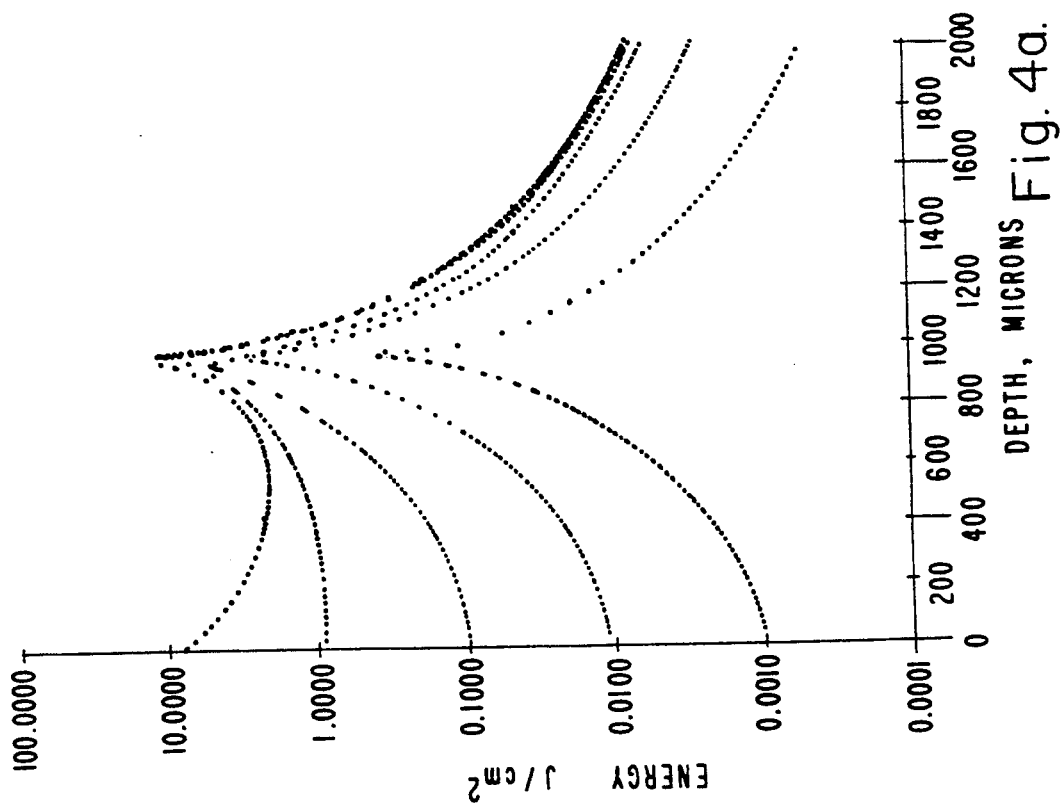

The approximate damage threshold for the material in solution is 10J/cm$^2$. FIGS. 4a and 4b show the effect of increasing the optical gain to 500 and 900 respectively. In FIG. 4a, the damage threshold of 10J/cm$^2$ is slightly exceeded near the center of the material, where in FIG. 4b it is substantially exceeded. For the optical gain of 500, the clamped output value is below 10 mJ/cm$^2$. This is in comparison to the case of the gain factor of 10, which has a limiting value of approximately 75 mJ/cm$^2$.

The clamped value of output energy decreases as the optical gain increases. This is because increasing the optical gain increases the local fluence in the material, causing more molecules to be turned on and participate in optical limiting through non-linear absorption. The limit to decreasing the output energy by simply increasing the optical gain is reached when either the peak fluence inside the material reaches a catastrophic level, or the number of molecules participating in non-linear absorption decreases to a level which cannot provide enough attenuation. The latter effect occurs when the beam is focused so tightly that the region in which the local fluence is above the non-linear absorption threshold is so narrow that an insufficient number of molecules exist in this space which can be turned on to absorb the required amount of energy from the light beam.

Up until this point the optical limiter acts in a self-protecting manner by limiting the maximum fluence inside the sample. This is due to the non-linear absorption shifting from the focal point toward the converging lens as the input energy increases. The shift in the maximum fluence region results from an increasing number of molecules between the focal point and the converging lens being turned on as the overall fluence level inside the material increases in response to the increased input energy.

In FIG. 4a, there is too much non-linear absorption occurring at the front of the material, and not enough near the center. This indicates that a further increase in optical gain to achieve a lower clamped output value is not possible with a uniform distribution of molecules in the material. The reason for this is, as discussed above, because the non-linear absorption region has become so narrow due to the high degree of optical gain and resulting beam convergence that the non-linear absorption effect of the material has reached saturation. Increasing the optical gain further, as illustrated in FIG. 4b, results in a higher, rather than a lower, maximum fluence in the material since the overall level of non-linear absorption has been decreased.

This limitation of the prior art is overcome in accordance with the present invention by distributing reverse saturable material in an absorbing body with a non-uniform concentration, which is maximum in the highest fluence region of the body around the focal point of the converged light beam, and decreases toward the converging lens. If desired, the concentration may further decrease from the maximum fluence region away from the converging lens. This non-uniform concentration distribution or gradient increases the number of molecules that are turned on for a particular value of optical gain, enables the optical gain to be substantially increased above the threshold limit inherent in a uniform distribution, and thereby limits the maximum fluence in the material and the output energy to lower values than are attainable with a uniform distribution of molecules.

Figure 5A:
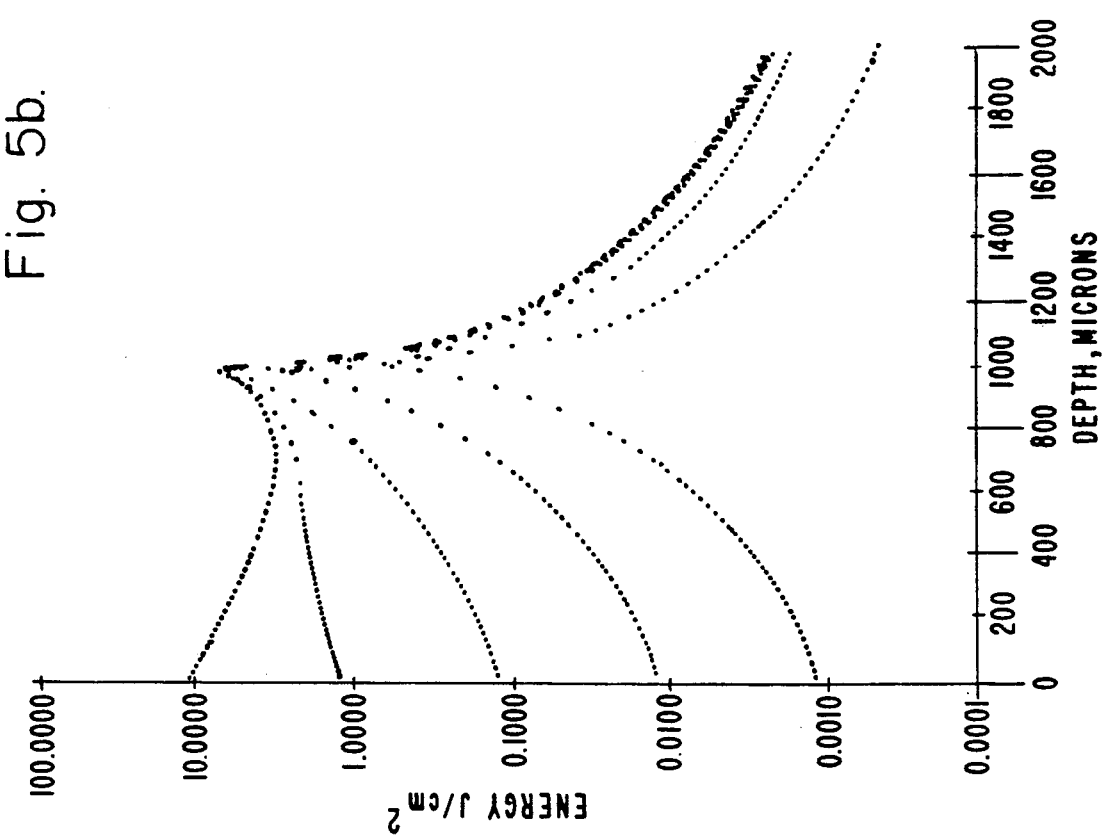
FIG. 5a is a graph illustrating a concentration gradient or distribution of a reverse saturable material according to the invention which is achievable using an indiffusion technique.

An example of such a distribution which is attainable using readily available technology is illustrated in FIG. 5a. The drawing illustrates an "indiffusion profile" which may be produced by allowing molecules of reverse saturable material to be absorbed into a porous or "thirsty" glass such as sol-gel. The concentration is equal to $N_0$ at the center of the material, and decreases exponentially to $N_0/e$ (where e is the base of natural logarithms) at the edges. In comparison with FIGS. 4a and 4b, it will be seen in FIG. 5b that the damage threshold of 10J/cm$^2$ is not exceeded, and that the output energy is clamped to approximately 1 mJ/cm$^2$ as compared to a value closer to 10 mJ/cm$^2$ for the uniform distribution. The shift in the maximum fluence region toward the converging lens is even greater with a non-uniform concentration distribution than with a uniform distribution, which further enhances the dynamic range and performance of the present optical limiter.

Figure 5B:
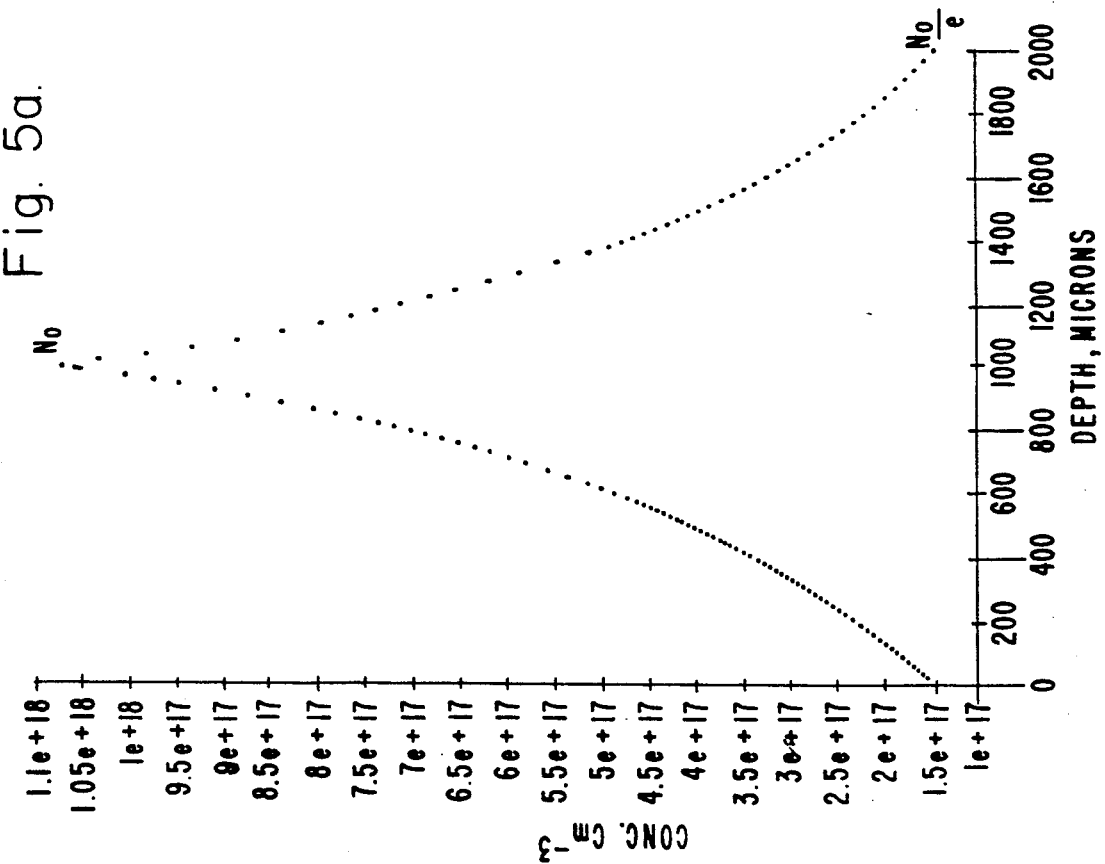
FIG. 5b illustrates reverse saturable absorption for a material having the concentration distribution shown in FIG. 5a and an optical gain factor of 900.

Whereas the exponential concentration distribution illustrated in FIGS. 5a and 5b substantially improves the optical limiting effect over a uniform distribution, the maximum benefit is obtained by distributing the molecular concentration in the reverse saturable material so as to correspond to the local optical gain in the material. This is achieved as illustrated in FIG. 6a by providing a concentration distribution according to the function $$N(Z) = N_0/[1 + ((d-Z)/Z_0)^X]$$

where $Z_0 = d/(G-1)^{\frac{1}{2}}$
for $0 < Z < d$ where $N_0$ is the maximum value of molecular concentration in the material, N is the local concentration, G is the optical gain of the converged light beam, d is the location of the point at which the concentration is equal to $N_0$ (in the maximum fluence region at the focal point of the converged light beam), $Z_0$ is the effective depth of field of the converging beam, Z is the displacement from the converging lens toward d, and X is a constant which varies according to the material and the optical gain G. This is the same function which describes the local optical gain in the material, with $X = 2$.

Where it is further desired that the concentration decrease symmetrically from the maximum value away from the converging lens, the thickness of the material will be $D = 2d$, and the concentration distributed according to the above function with the displacement Z measured from the converging lens toward d.

Figure 6B:
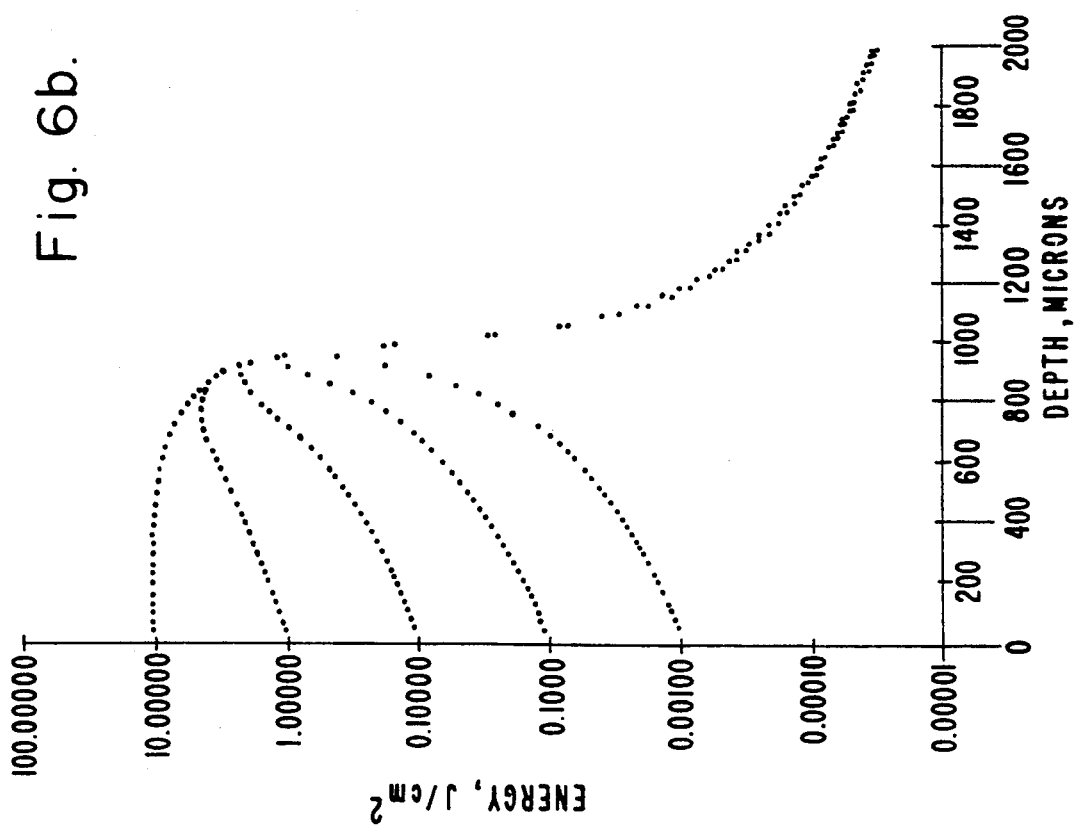
FIG. 6b is a graph illustrating reverse saturable absorption for the material shown in FIG. 6a, and an optical gain factor of 5000.
Figure 6A:
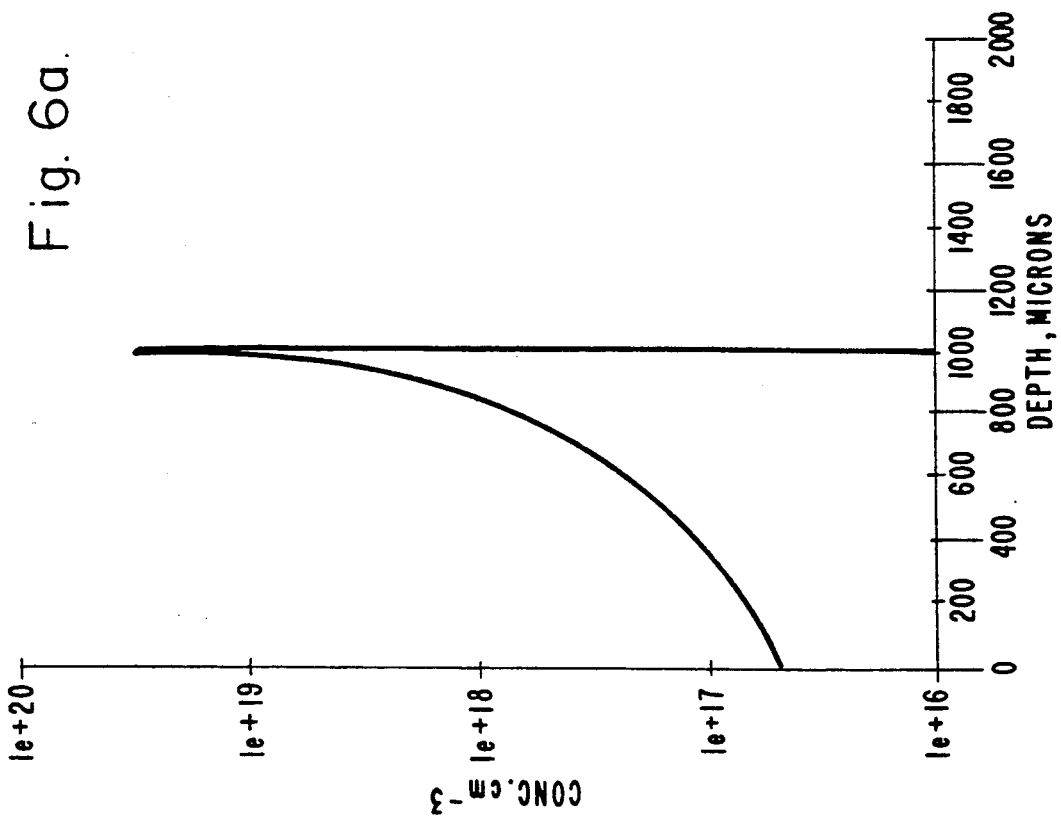
FIG. 6a is a graph illustrating a preferred concentration distribution according to the present invention.

The computer solution for the above function for the exemplary iron tricobalt deca-carbonyl bistrimethyl phosphine material with $N_0 = 10^{19}$ (chosen for 50% linear absorption) and $X = 1.5$ is illustrated in FIG. 6b. The local energy does not exceed the damage threshold of 10J/cm$^2$, even at an optical gain of 5000. The clamped output value is approximately 35 $\mu$J/cm$^2$, yielding a dynamic range of approximately 55 dB. This is in comparison with approximately 30 dB for the uniform distribution. The increased self-protecting action is clearly seen as the peak fluence strongly moves toward the source for increasing values of input energy.

EXAMPLE

Figure 7A:
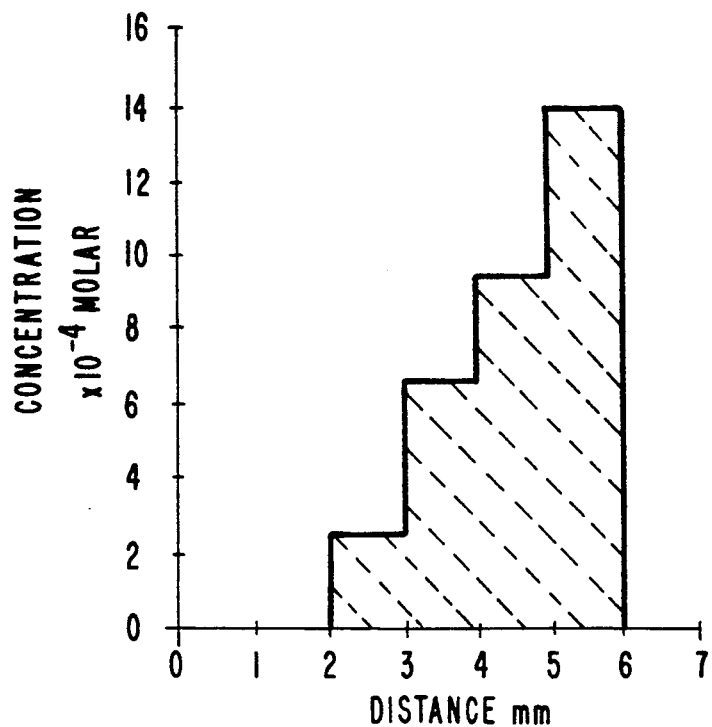
FIG. 7a illustrates a concentration distribution which varies in a stepwise manner and FIG. 7b is a diagram illustrating an optical limiting body constructed in accordance with an example of the invention.
Figure 7B:
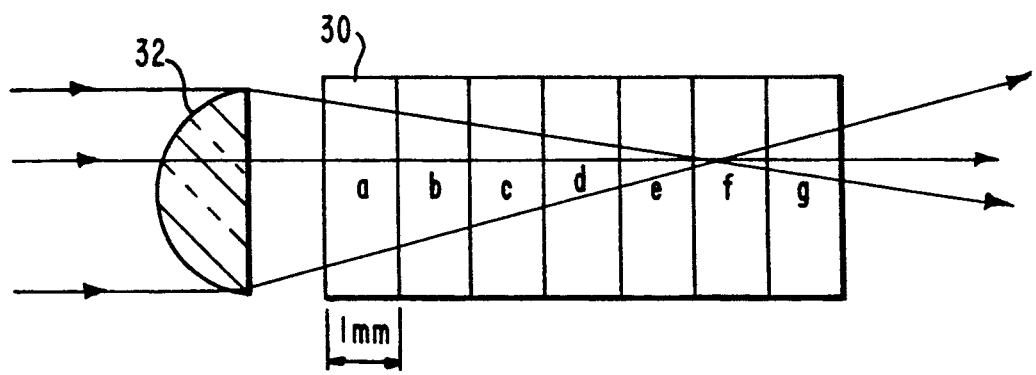

Although optimal performance is obtained with a continuous concentration gradient which corresponds to the local optical gain as described above, the present invention may be advantageously practiced using a concentration distribution which varies in a stepwise manner as shown for example in FIG. 7a. A nonlinear light absorbing sample 30 illustrated in FIG. 7b was fabricated with a maximum concentration of reverse saturable material located at the focal point of a converging lens 32 having an effective back focal length of 7.25 mm. The material was cyclopentadienyl iron carbonyl tetramer, also known as King's complex, which is a preferred material for practicing the invention.

Figure 9:
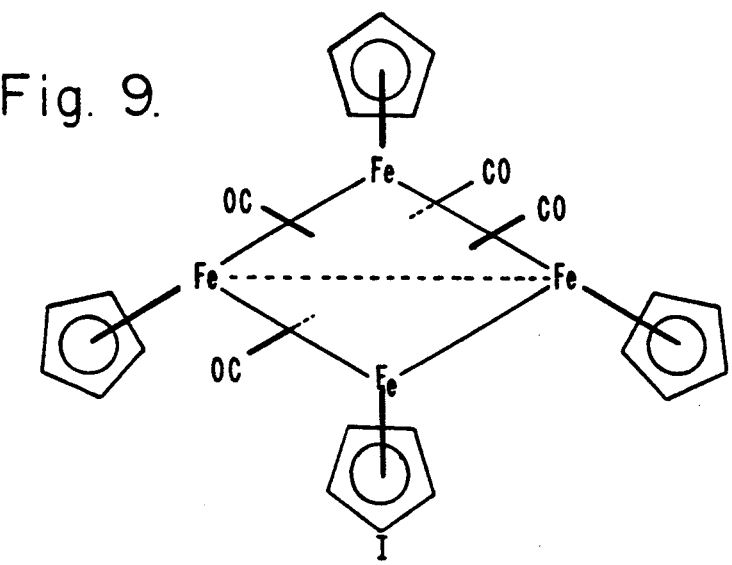
FIG. 9 is a diagram illustrating the chemical structure of a material used in the body of FIG. 7b.

Cyclopentadienyl iron carbonyl tetramer is a known compound described in various publications such as R. B. King, "Organometallic chemistry of the Transition Metals, XVI, Polynuclear Cyclopentadienyl metal Carbonyls of Iron and Cobalt", *Inorganic Chemistry*, Vol. 5, no. 12, December 1966, pp. 2227–2230, and whose structure is depicted in FIG. 9 of the present application. One approach to synthesizing the tetramer is described in this publication, but a preferred approach is described in White and Cunningham, "Synthesis and Electrochemistry of Cytlopentadienylcarbonyliron Tetramer", *J. Chemical Education.* vol. 57, no. 4 (1980), pp. 317.

The material was incorporated into the polymer polymethyl-methacrylate (PMMA), also known as lucite or plexiglass. Wafers a to g having a thickness of 1 mm and different molecular concentrations were fused together to produce the 7 layer step graded sample 30. The transmittance values for the wafers were a=100%, b=100%, c=93%, d=82%, e=78%, f=70%, and g=100%. The calculated transmittance through the sample was 42%, whereas the measured transmittance was 45%.

The individual wafers were cut from 1 cm diameter by 1 cm long boules, and each face was polished using conventional optical polishing techniques. The transmission for each sample was individually measured, and the wafers were fused together by applying a thin film of unpolymerized PMMA and allowing the film to cure.

Figure 8:
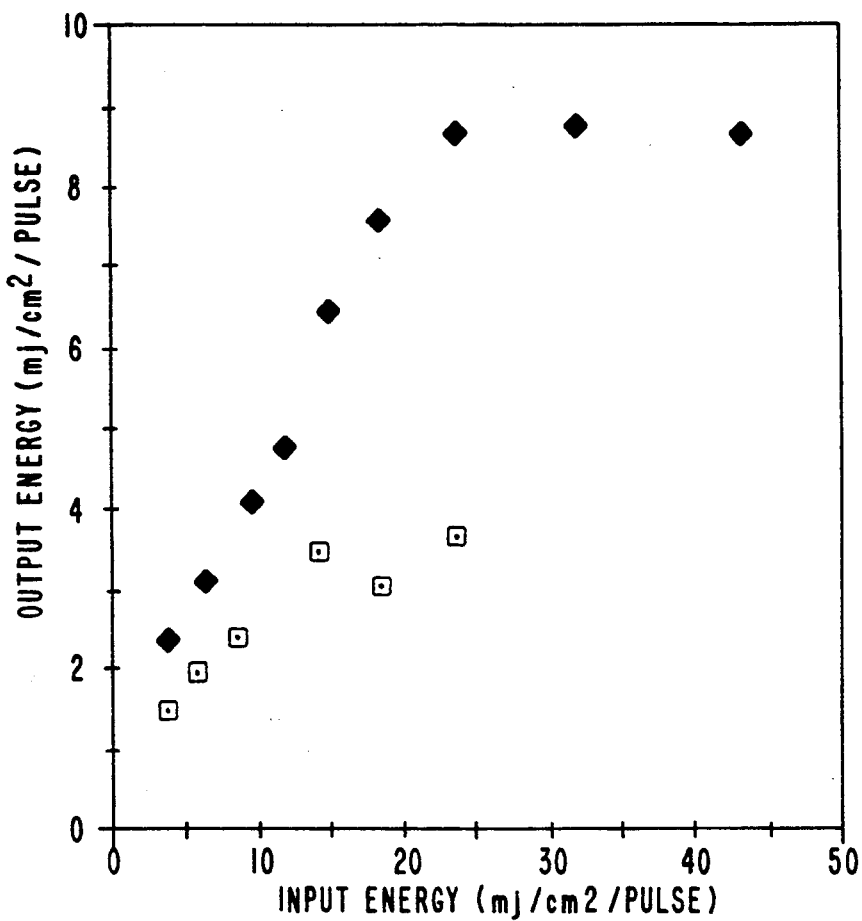
FIG. 8 is a graph illustrating experimental data obtained with the body of FIG. 7b.

As illustrated in FIG. 8, the optical limiting properties of the step graded sample were measured and compared to the optical limiting properties of a homogeneous distribution of molecules in liquid. For the homogeneous solution, the molecules were dissolved in methylene chloride and placed in a 1 cm thick quartz spectrophotometer cell. The transmissions for the solution and sample were within experimental error, and equal to 45%. The optical limiting measurements were taken at the same time using essentially identical experimental conditions. The results are illustrated in FIG. 8, which clearly shows the graded distribution limiting at lower thresholds of input energies, and having lower clamped output limiting energies. The output limiting energies for the graded distribution were near the minimum measurement capabilities of the experimental apparatus. Therefore, the data is slightly scattered compared to the data for the homogeneous solution.

While several illustrative embodiments of the invention have been shown and described, numerous variations and alternate embodiments will occur to those skilled in the art, without departing from the spirit and scope of the invention. Accordingly, it is intended that the present invention not be limited solely to the specifically described illustrative embodiments. Various modifications are contemplated and can be made without departing from the spirit and scope of the invention as defined by the appended claims.

We claim:

1. An optical limiter, comprising:
   a light absorbing body including a material having reverse saturable optical absorption; and
   optical converging means for converging a light beam into the absorbing body;
   the material having a non-uniform concentration with a maximum value in a region of the body in which the fluence of the converged light beam is maximum.

2. An optical limiter as in claim 1, in which the converging means is constructed to converge the light beam to a focal point in said region of the body.

3. An optical limiter as in claim 1, in which said concentration decreases from said maximum value in said region of the body toward the converging means.

4. An optical limiter as in claim 3, in which said concentration further decreases from said maximum value in said region of the body away from the converging means.

5. An optical limiter as in claim 3, in which the converging means is constructed to converge the light beam in accordance with a predetermined optical gain function, said concentration decreasing in a manner which approximates said optical gain function.

6. An optical limiter as in claim 3, in which the converging means is constructed to converge the light beam in accordance with a predetermined optical gain function, said concentration decreasing in a manner which corresponds to said optical gain function.

7. An optical limiter as in claim 1, in which said concentration decreases from said maximum value at a point in said region in the body toward the converging means substantially in accordance with the function $N(Z)=N_0/[1+((d-Z)/Z_0)^x]$, with $Z_0=d/(G-1)^{\frac{1}{x}}$, where $N_0$ is said maximum value, N is said concentration, G is the optical gain of the light beam in the body, d is the location of said point, $Z_0$ is the effective depth of field of the light beam in the body, Z is the displacement from the converging lens toward d, and X is a constant which varies according to the material and the optical gain G.

8. An optical limiter as in claim 7, in which the material comprises iron tricobalt deca-carbonyl bistrimethyl phosphine, X is approximately 1.5, and $N_0$ is approximately $10^{19}$.

9. An optical limiter as in claim 1, in which the material comprises cyclopentadienyl iron carbonyl tetramer.

10. An optical limiter as in claim 7, in which said point is the focal point of the converged light beam.

11. An optical limiter as in claim 1, in which the converging means comprises a converging lens.

12. An optical limiter for optically limiting the fluence of a light beam propagating therethrough to a predetermined maximum value, comprising:
   a light absorbing body including a material having reverse saturable optical absorption, the material having a non-uniform concentration in the body; and
   optical converging means for converging the light beam into the absorbing body with a predetermined optical gain;
   the material, non-uniform concentration, and predetermined optical gain being selected such that the fluence of the converged light beam is limited to said predetermined maximum value by reverse saturable optical absorption in the material.

13. An optical limiter as in claim 12, in which the non-uniform concentration is selected such that the material produces a self-protecting effect by causing a region of maximum fluence of the converged light beam therein to shift toward the converging means as the input energy of the light beam increases.

14. An optical limiter as in claim 13, in which said concentration decreases from a region of maximum fluence of the converged light beam in the body toward the converging means.

15. An optical limiter as in claim 14, in which said concentration decreases in correspondence with the local value of optical gain in the material.

16. An optical limiter as in claim 12, in which said concentration decreases from a maximum value at a point in a region of maximum fluence of the converged light beam in the body toward the converging means substantially in accordance with the function $N(Z)=N_0/[1+((d-Z)/Z_0)^x]$, with $Z_0=d/(G-1)^{\frac{1}{2}}$, where $N_0$ is said maximum value, N is said concentration, G is the optical gain of the light beam in the body, d is the location of said point, $Z_0$ is the effective depth of field of the light beam in the body, Z is the displacement from the converging lens toward d, and X is a constant which varies according to the material and the optical gain G.

17. An optical limiter as in claim 12, in which the converging means comprises a converging lens.

18. An optical limiter as in claim 12, in which the material, non-uniform concentration, and optical gain are further selected to limit the output energy of the light beam to a predetermined maximum value.

19. An optical limiter as in claim 12, in which the material comprises cyclopentadienyl iron carbonyl tetramer.

20. An optically limiting body including a material having reverse saturable optical absorption, the material having a non-uniform concentration with a maximum value at a predetermined point in the body, said concentration decreasing toward a light receiving surface of the body, in which said concentration decreases substantially in accordance with the function $N(Z)=N_0/[1+((d-Z)/Z_0)^x]$, with $Z_0=d/(G-1)^{\frac{1}{2}}$, where $N_0$ is said maximum value, N is said concentration, G is the optical gain of the light beam in the body, d is the location of said point, $Z_0$ is the effective depth of field of the light beam in the body, Z is the displacement from the converging lens toward d, and X is a constant which varies according to the material and the optical gain G.

21. A body as in claim 20, in which the material comprises iron tricobalt deca-carbonyl bistrimethyl phosphine, X is approximately 1.5, and $N_0$ is approximately $10^{19}$.

22. An optically limiting body including a material having reverse saturable optical absorption, the material having a non-uniform concentration with a maximum value at a predetermined point in the body, said concentration decreasing toward a light receiving surface of the body in which the material comprises cyclopentadienyl iron carbonyl tetramer.

* * * * *